United States Patent [19]

Bringhurst et al.

[11] Plant 4,679

[45] Mar. 31, 1981

[54] STRAWBERRY PLANT

[75] Inventors: Royce S. Bringhurst, Davis; Victor Voth, Santa Ana, both of Calif.

[73] Assignee: The Regents of the University of California, Berkeley, Calif.

[21] Appl. No.: 92,020

[22] Filed: Nov. 7, 1979

[51] Int. Cl.[3] ..... A01H 5/00
[52] U.S. Cl. ..... Plt./48
[58] Field of Search ..... Plt./48

*Primary Examiner*—James R. Feyrer
*Attorney, Agent, or Firm*—Townsend and Townsend

[57] ABSTRACT

A new and distinct variety of strawberry plant of a day-neutral type characterized by its ability after winter and spring plantings in Central California to produce fruit three months after planting continuously on a cyclic basis throughout summer and fall. The variety is also characterized by its runner prolificacy in the nursery; its ability to flower and fruit at any time independent of day length with minimum conditioning and its fruit which is firm and durable, medium long, blunt-ovoid to wedge-shaped and sometimes hollow centered. The fruit is larger in size than Tioga and has an excellent flavor similar to that of Sequoia.

3 Drawing Figures

DESCRIPTION

This invention relates to a new and distinctive day-neutral type cultivar designated Aptos, which resulted from a cross between Cal. 65.63–601 (not patented), a second generation backcross (to Sequoia, U.S. Plant Pat. No. 3,178) derivative from *Fragaria Virginiana Glauca* from Utah and Tufts (U.S. Plant Pat. No. 3,561) as follows:

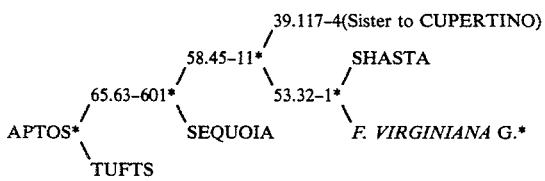

*Indicates source of day-neutral trait.

Aptos first fruited at the Wolfskill Experimental Orchards of the University of California near Davis in 1971, where it was selected in 1972 and designated originally as Cal. 70.7–130; and Aptos has been asexually reproduced by runners at Davis, Calif., and later tested as CN15.

Aptos has been tested with varying results at various University of California field stations and facilities and to a limited extent in representative growers' fields, under strict control. Meristem originated, virus negative stock has been developed by the University of California.

FIG. 1 of the accompanying drawing shows typical growth, flowering and fruiting characteristics.

Figure 1:
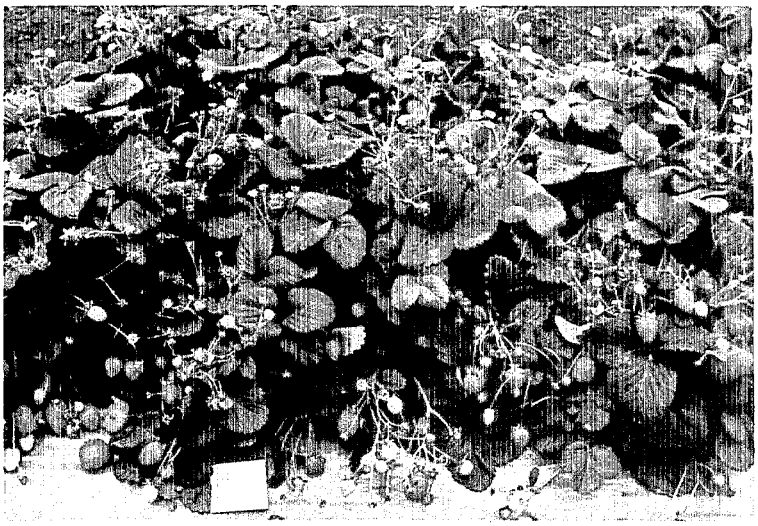
Figure 2:
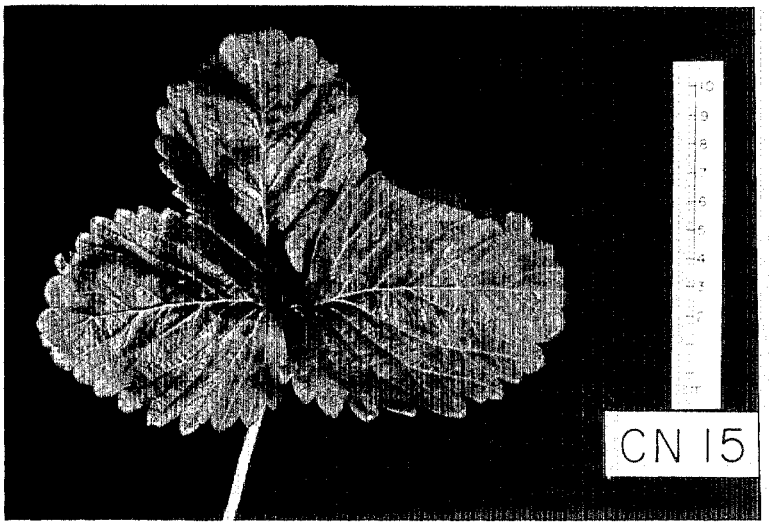
FIG. 2 shows a typical mid-summer mature leaf from a spring planted plant.
Figure 3:
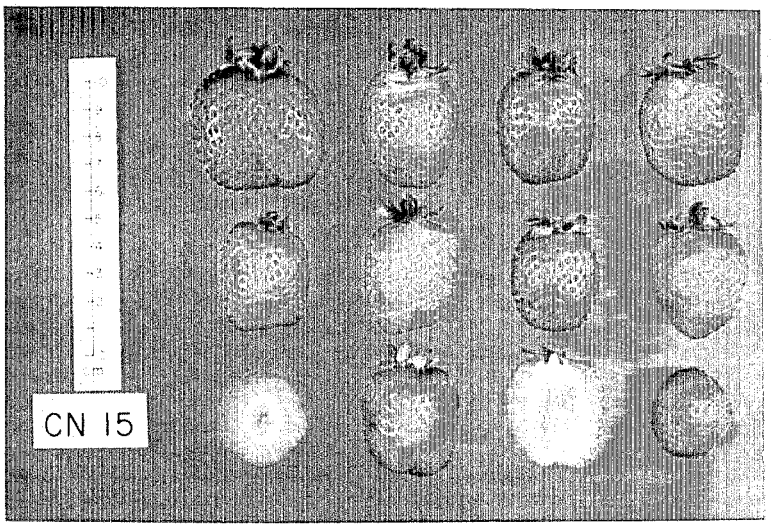
FIG. 3 shows representative mid-season fruit of Aptos with longitudinal and cross sectional views.

Aptos has performed well in summer fruiting experiments with winter and spring planted plants in Central California but much less satisfactorily in winter fruiting experiments with summer planted plants in Southern California, where it is not as early as might be desired. Spring and summer fruit can be produced continuously on a cyclic basis throughout summer and fall beginning about three months after planting.

The distinctive characteristics of this new strawberry cultivar, described below, were observed upon discovery and/or through the test period.

Plants and foliage: Aptos plants are erect in growth habit, somewhat similar to Tufts. On the average, plants are somewhat smaller than those of Tufts or Tioga but larger than those of Aiko. Bract leaves do not normally occur on Aptos in contrast to important California short-day cultivars. Leaflets of Aptos are somewhat larger than those of Tioga or Tufts and are about the same color as those of Tioga, 2.5 GY 4/3 (Munsell Color System—Nickerson Color Fan). Leaflets of Aptos have about the same number of serrations as those of Tioga or Aiko (±10/half blade), fewer than Tufts (±12) as averaged over the half blades of the three leaflets on mid-season mature leaves at Watsonville. Aptos plants are vigorous and prolific runner makers in the nursery. Runner production in the fruiting beds also occurs at varying rates throughout the summer and the runner plants always flower within a relatively short time, whether rooted or not. Aptos plants have a relatively low chilling requirement and will fruit in the winter under adequate temperature conditions.

Isozymes in leaf extracts: Aptos is distinctive from the important California cultivars compared over three enzyme systems: A. Phosphoglucoimerase (PGI); B. Leucine amino peptidase (LAP); and, C. Phosphoglucomutase (PGM) (Scandalios, 1969. Biochem. Genet. 3:37).

| | TIOGA | TUFTS | AIKO | APTOS |
|---|---|---|---|---|
| PGI* | A1 | A2 | A4 | A4 |
| LAP* | B1 | B3 | B3 | B3 |
| PGM* | C3 | C4 | C2 | C3 |

*Patterns described in detail elsewhere.

Flowering and fruiting: Aptos is a new type of California strawberry cultivar in that with a minimum of conditioning it will flower and fruit anytime, effectively independent of day length. The inflorescences are very long and similar to those of Tufts. The flowers are self fertile with ample pollen throughout the season.

Fruit appearance: Aptos has medium long, blunt-ovoid to wedged fruit, sometimes hollow centered. The fruit skin color, about 5.5 R 4.5/13 (ibid.), is distinctly redder than those of Tioga (7.5 R 4.5/13), turning dark and dull when overripe, similar to Sequoia. The flesh color is similar to that of the skin with a light ring around the core. The achenes are slightly embedded, similar to Aiko. The calyx is small and usually reflexed (similar to Tufts). Aptos fruit is about as firm and durable as that of Tioga, Tufts or Aiko, according to penetrometer readings and handling comparisons. Average fruit size compare favorably with Aiko, somewhat smaller than Tufts but larger than Tioga.

Fruit quality: Ascorbic Acid: Aptos has averaged ±57 mg/100 g. of fresh fruit, much greater than Tioga (±40) or Tufts (±45) and only slightly less than Aiko (±60) as tested by the method of Loeffler and Ponting (1942, J. Indust. and Engin. Chem. 14:846). Soluble Solids: Aptos averaged ±8.0, not significantly different from Tioga, Tufts or Aiko, taken at the same place at the same time. The flavor of Aptos is very similar to that of Sequoia, excellent in our opinion and according to that of most who have tried it. It should be considered for fresh market, processing and home gardening.

We claim:

1. The new and distinct variety of strawberry plant herein described and illustrated and identified by the characteristics enumerated above.

* * * * *

UNITED STATES PATENT AND TRADEMARK OFFICE

CERTIFICATE OF CORRECTION

PATENT NO. : Plant 4,679

DATED : March 31, 1981

INVENTOR(S) : Bringhurst, et al.

It is certified that error appears in the above-identified patent and that said Letters Patent is hereby corrected as shown below:

Column 2, line 35, in the subcolumn corresponding to the cultivar Aptos, delete "C3" and substitute --C4--.

Signed and Sealed this

Thirty-first Day of March, 1992

*Attest:*

HARRY F. MANBECK, JR.

*Attesting Officer*

*Commissioner of Patents and Trademarks*